United States Patent [19]

Kook

[11] 3,943,243
[45] Mar. 9, 1976

[54] TOILET BOWL SANITIZER AND BATHROOM DEODORIZER
[75] Inventor: John F. Kook, Parma, Ohio
[73] Assignee: E. I. Du Pont de Nemours and Co., Wilmington, Del.
[22] Filed: Oct. 19, 1972
[21] Appl. No.: 298,836

Related U.S. Application Data
[63] Continuation-in-part of Ser. No. 814,710, April 9, 1969, abandoned.

[52] U.S. Cl.................................. 424/76; 424/164
[51] Int. Cl............................................. A61l 13/00
[58] Field of Search............................ 424/76, 164

[56] References Cited
FOREIGN PATENTS OR APPLICATIONS
567,002   1/1945   United Kingdom................ 424/164

OTHER PUBLICATIONS
Hackh's Chemical Dictionary, 3rd. Ed., McGraw Hill Book Co., Inc., N.Y., p. 779, (1944).

Primary Examiner—Stanley J. Friedman

[57] ABSTRACT
Compositions containing sodium bisulfate and p-dichlorobenzene or naphthalene are useful as sanitizers for toilets and their surrounding environments.

2 Claims, 4 Drawing Figures

TOILET BOWL SANITIZER AND BATHROOM DEODORIZER

CROSS-REFERENCE TO RELATED APPLICATIONS

This application is a continuation-in-part of my co-pending application Ser. No. 814,710, filed Apr. 9, 1969, now abandoned.

DESCRIPTION OF THE INVENTION

General

This invention relates to compositions which can be used as sanitizers for toilets and their surrounding environments.

In the past, sodium bisulfate has been used to clean toilets, for example, see U.S. Pat. No. 1,865,948; U.S. Pat. No. 1,885,390; U.S. Pat. No. 2,034,070; U.S. Pat. No. 2,497,057 and U.S. Pat. No. 3,318,815. Generally solid particles of sodium bisulfate are placed in the toilet bowl and allowed to dissolve after which the bowl is scrubbed with an ordinary toilet bowl scrub brush. No convenient manner has been heretofore known whereby sodium bisulfate could be supplied to the toilet bowl on a continuous basis. It has been discovered that sodium bisulfate can be supplied on a continuous basis at a slow rate to a toilet bowl while at the same time providing a pleasant odor throughout the environment of the toilet.

The objectives of this discovery are accomplished by placing a solid composition comprising:

A. 10% to 65%, by weight, of sodium bisulfate, and
B. 90% to 35%, by weight, of p-dichlorobenzene, or naphthalene or a mixture of the two, within a toilet bowl above the water line. The solid composition may be placed such that it does or does not come into contact with flushing water.

DRAWINGS

Figure 1:
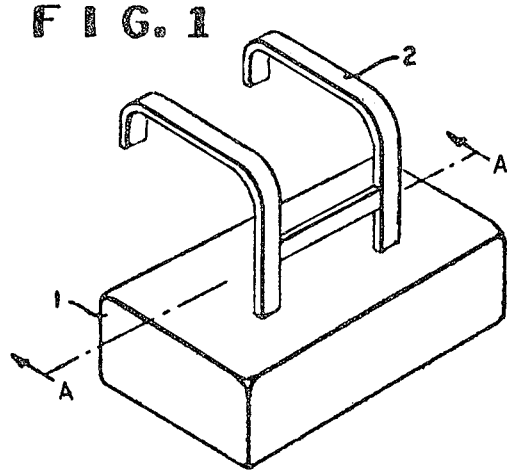

FIG. 1 illustrates an embodiment of this invention. Solid composition 1 contains sodium bisulfate and p-dichlorobenzene or naphthalene. Holder means 2, partially inserted in the composition, is used to fasten the composition to the toilet. The holder means may be made from any suitable materials, such as plastics or metals.

Figure 2:
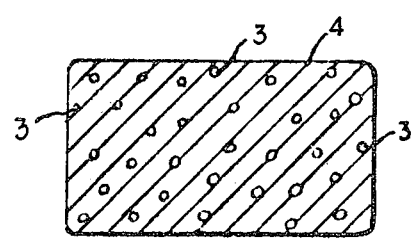

FIG. 2 is a cross section through A–A' of composition 1 in FIG. 1. Solid particles of sodium bisulfate 3 are dispersed through the naphthalene or p-dichlorobenzene 4. As p-dichlorobenzene or naphthalene evaporates, sodium bisulfate either contacts flushing water and dissolves therein or merely falls into the bowl. Dissolved sodium bisulfate bleaches the toilet bowl thereby cleaning same.

Figure 3:
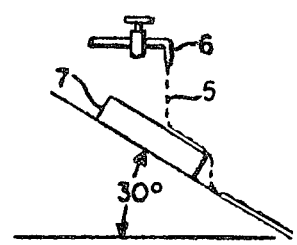

FIG. 3 is described in Example 4 hereinafter.

Figure 4:
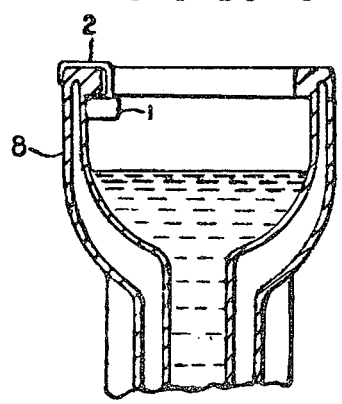

FIG. 4 is a cross section of a toilet in which sanitizer 1 is shown attached to toilet 8 by holder 2.

METHOD FOR PREPARING COMPOSITIONS

The compositions of this invention are made from sodium bisulfate and p-dichlorobenzene or naphthalene or a mixture of the two.

Sodium bisulfate is a generally white solid which readily dissolves in water and has the chemical formula $NaHSO_4$. The chemical is readily available commercially, being sold under the trademark "G B S" by E. I. du Pont de Nemours and Company. Any suitable form of sodium bisulfate may be used. A preferred sodium bisulfate source is one wherein the particles have a particle size between about 10 and 100 U.S. mesh (0.0787 inch and 0.0059 inch, respectively) and an average particle size between 30 and 40 U.S. mesh (0.0232 inch and 0.0164 inch, respectively).

The second ingredient can be p-dichlorobenzene which is an organic chemical having the general formula

and which melts at about 53.1°C. The chemical is available commercially being sold under the trademark "Para Dow" by the Dow Chemical Company. Evaporation of this chemical provides pleasant odors; and it has been employed in slow dissolving sanitizing tablets, see U.S. Pat. No. 3,496,269. The use of p-dichlorobenzene is preferred.

The second ingredient can also be naphthalene or a mixture of p-dichlorobenzene and naphthalene. Naphthalene is a white crystalline material and is available commercially.

The compositions can be made by the following steps. Into a mold of suitable size, e.g., 3 inches × 2 inches × 1 inch, is placed solid p-dichlorobenzene. The mold is then heated to a temperature sufficient to melt the p-dichlorobenzene, e.g. 55°–60°C. Thereafter, solid particles of sodium bisulfate are added to the mold. At this point the mold is allowed to partially cool. Just prior to the time the p-dichlorobenzene solidifies, the mixture is stirred or agitated to evenly disperse the solid particles of sodium bisulfate throughout the p-dichlorobenzene. After stirring, a suitable means for holding is inserted into the composition. Finally, the p-dichlorobenzene is allowed to completely solidify. Naphthalene or a mixture of the two can also be used in this melt forming step.

Alternatively the sodium bisulfate and p-dichlorobenzene or naphthalene can be compacted into a shaped, solid composition by use of a compactor, press, or the like.

The solid composition can be in various shapes, i.e., it can be shaped as a cake, brick, cube, rectangle, cylinder, sphere, prism, etc. In this description and the claims the term "shaped form" will be used to define these various shapes. It is an important feature of the invention that the composition be solidified or compressed into this shaped form.

The weight percentages of sodium bisulfate should be such that 10% to 65% of the total amount of the solid composition is sodium bisulfate. If larger amounts of sodium bisulfate are used, the composition will not have a sufficient amount of p-dichlorobenzene or naphthalene to form a cake and the mixture will generally be an agglomerated mass of particles which readily breaks apart. If smaller amounts of sodium bisulfate are used, there probably will not be sufficient sodium bisulfate to accomplish the desired cleaning effect.

Other materials commensurate with the objectives of the invention may be added to the composition. Such materials include sodium benzene sulfochloramide (a chlorine bleaching agent), potassium peroxysulfate (oxygen bleaching compound), scented fragrances, and/or coloring matter, e.g., dyes.

The compositions of this invention provide for the continuous release of the sodium bisulfate at a slow rate, i.e., the composition, will generally last between 14–30 days depending on the amount of flushing required. In the absence of combining it in the solid, shaped form, with the p-dichlorobenzene or naphthalene, the sodium bisulfate would be used at a much higher rate.

The following examples illustrate the preparation and use of the compositions of this invention. Parts are by weight unless otherwise stated.

EXAMPLE 1

One part of p-dichlorobenzene is heated in a mold 3 × 2 × 1 inch to about 60°C. until it melts. Thereafter, 1 part of sodium bisulfate (average particle size about 30 U.S. mesh) is added to the p-dichlorobenzene. The mold contents are allowed to partially solidify. Just before the p-dichlorobenzene solidifies, the composition is stirred to disperse the solid particles of sodium bisulfate and a suitable plastic holder, as shown in FIG. 1, is inserted into the mold. The p-dichlorobenzene is allowed to solidify at room temperature. The article is then placed in a toilet bowl where it is contacted with water upon each flushing. The toilet is flushed on the average of about 6 times per day. The cake lasts 22 days after which there is a very slight build-up above the water level which is easily removed by brushing. Throughout the 22 days, a pleasant odor is observed by humans in the environment of the toilet.

One part of naphthalene can be substituted for the p-dichlorobenzene to produce a shaped form useful as a toilet bowl sanitizer and deodorizer.

EXAMPLE 2

A sanitizer is made in accordance with Example 1 except that 0.8 part of p-dichlorobenzene and 1.2 parts of sodium bisulfate is used. The resulting cake performs in essentially the same manner as that of Example 1 except that it lasts only 20 days.

EXAMPLE 3

A sanitizer is made in accordance with Example 1 except that 1.8 parts of p-dichlorobenzene and 0.2 part of sodium bisulfate is used. The resulting cake performs in essentially the same manner as that of Example 1 except that it lasts 26 days.

EXAMPLE 4

This example shows the solubility rates of sodium bisulfate at different concentrations. Solid cakes of sodium bisulfate and p-dichlorobenzene are prepared by melting the p-dichlorobenzene and adding thereto sodium bisulfate (average particle size about 30 U.S. mesh) followed by solidification. Cakes were prepared containing 10%, 25%, 50%, and 100% sodium bisulfate, the latter being prepared by melting sodium bisulfate and solidifying. Each cake is weighed and subjected to water treatment as shown in FIG. 3 where water 5 from faucet 6 is allowed to flow at a rate of 0.2 cu. ft./min. over cake 7 secured at a 30° angle to horizontal. The results are as follows:

| % $NaHSO_4$ in Cake | Cake Size Inches | Time Minutes | Weight Loss Grams |
|---|---|---|---|
| 10 | 2-1/8 × 1-9/16 × 1/4 | 10 | 0.1 |
| 25 | 2 × 1-11/16 × 1/4 | 10 | 0.8 |
| 50 | 2-1/8 × 1-3/4 × 3/16 | 10 | 1.0 |
| 100 | 2 × 1-7/8 × 3/16 | 1.25 | 16.15 |

As can be seen from the data, the solubility rate of sodium bisulfate is reduced as the percentage of p-dichlorobenzene is increased. The cakes having 10%, 25%, and 50% sodium bisulfate can be used as sanitizers. The amount of sodium bisulfate in any given sanitizer will depend upon the amount of cleaning required. In a toilet having light flushing requirements, cakes with small percentages (10–30%) of sodium bisulfate should be used. If, however, heavy flushing requirements exist, cakes with high percentages (50–65%) of sodium bisulfate should be used.

The solid, shaped forms of the compositions of this invention may also be used to control pH of water. The compositions release acid in water and thus will control algae in cooling towers and ponds. The compositions when placed in water containing soluble calcium and barium salts will precipitate same as sulfates.

Sodium bisulfate can cause skin irritation. Paradichlorobenzene is poisonous. Accordingly, it is desirable when using the sanitizers of this invention to be careful children do not come in direct contact with the solid, shaped forms.

I claim:

1. A method for continuously dispensing sodium bisulfate at a slow rate to a toilet while at the same time providing a pleasant odor in the environment of the toilet by placing in the bowl of said toilet, above the water line, a shaped solid in the form of a cake having a composition comprising:
   A. 10% to 65%, by weight, of sodium bisulfate, and
   B. 90% to 35%, by weight, of p-dichlorobenzene or naphthalene or a mixture of the two.

2. The method of claim 1 wherein p-dichlorobenzene is employed.

* * * * *